(12) United States Patent
Krueger et al.

(10) Patent No.: US 8,420,809 B2
(45) Date of Patent: Apr. 16, 2013

(54) PROCESS FOR THE MANUFACTURING OF BETAMIMETICS

(75) Inventors: Thomas Krueger, Kisslegg (DE); Uwe Ries, Biberach (DE); Juergen Schnaubelt, Oberhoefen-Warthausen (DE); Werner Rall, Mittelbiberach (DE); Zeno A. Leuter, Weingarten (DE); Adil Duran, Rissegg (DE); Rainer Soyka, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/021,946

(22) Filed: Feb. 7, 2011

(65) Prior Publication Data

US 2011/0124859 A1    May 26, 2011

Related U.S. Application Data

(63) Continuation of application No. 11/463,703, filed on Aug. 10, 2006, now abandoned.

(30) Foreign Application Priority Data

Aug. 15, 2005    (EP) .................................... 05107470

(51) Int. Cl.
    *C07D 265/36* (2006.01)
(52) U.S. Cl.
    USPC ........................................................ 544/105
(58) Field of Classification Search .................... 544/105
    See application file for complete search history.

(56) References Cited

U.S. PATENT DOCUMENTS

| | | | |
|---|---|---|---|
| 4,215,119 A | 7/1980 | Mentrup et al. |
| 4,252,951 A | 2/1981 | Jackson et al. |
| 4,460,581 A | 7/1984 | Schromm et al. |
| 4,570,630 A | 2/1986 | Elliott et al. |
| 4,656,168 A | 4/1987 | Atkinson et al. |
| 5,035,237 A | 7/1991 | Newell et al. |
| 5,223,614 A | 6/1993 | Schromm et al. |
| 5,472,143 A | 12/1995 | Bartels et al. |
| 5,497,944 A | 3/1996 | Weston et al. |
| 5,502,078 A | 3/1996 | Holloway et al. |
| 5,750,701 A | 5/1998 | Beeley et al. |
| 5,753,417 A | 5/1998 | Ulrich |
| 5,911,851 A | 6/1999 | Bartels et al. |
| 5,947,118 A | 9/1999 | Hochrainer et al. |
| 5,955,058 A | 9/1999 | Jager et al. |
| 5,964,416 A | 10/1999 | Jaeger et al. |
| 5,998,430 A | 12/1999 | Schwantes et al. |
| 6,007,676 A | 12/1999 | Bartels et al. |
| 6,176,442 B1 | 1/2001 | Eicher et al. |
| 6,453,795 B1 | 9/2002 | Eicher et al. |
| 6,491,897 B1 | 12/2002 | Freund et al. |
| 6,503,362 B1 | 1/2003 | Bartels et al. |
| 6,582,678 B2 | 6/2003 | Staniforth |
| 6,706,726 B2 | 3/2004 | Meissner et al. |
| 6,747,154 B2 | 6/2004 | Brandenburg et al. |
| 6,846,413 B1 | 1/2005 | Kadel et al. |
| 6,905,239 B2 | 6/2005 | Boeck et al. |
| 6,951,888 B2 | 10/2005 | Buettner et al. |
| 7,056,916 B2 | 6/2006 | Konetzki et al. |
| 7,084,153 B2 | 8/2006 | Banholzer et al. |
| 7,135,500 B2 | 11/2006 | Konetzki et al. |
| 7,160,882 B2 | 1/2007 | Bouyssou et al. |
| 7,220,742 B2 | 5/2007 | Lustenberger et al. |
| 7,244,728 B2 | 7/2007 | Bouyssou et al. |
| 7,244,742 B2 | 7/2007 | Pieper et al. |
| 7,273,603 B2 | 9/2007 | Schmidt |
| 7,307,076 B2 | 12/2007 | Konetzki et al. |
| 7,332,175 B2 | 2/2008 | Konetzki |
| 7,375,104 B2 | 5/2008 | Bouyssou et al. |
| 7,417,051 B2 | 8/2008 | Banholzer et al. |
| 7,423,036 B2 | 9/2008 | Konetzki et al. |
| 7,429,583 B2 | 9/2008 | Bouyssou et al. |
| 7,491,719 B2 | 2/2009 | Lustenberger et al. |

(Continued)

FOREIGN PATENT DOCUMENTS

CA    1180012 A    12/1984
CA    2164222 C    12/1994

(Continued)

OTHER PUBLICATIONS

Armarego, W. L. F.; Purification of Laboratory Chemicals (4th Edition); (1997) p. 529; Elsevier Publisher.
Babin, D. et al; A Biomimetic Synthesis of Chrysanthemol; (1981) vol. 37. No. 2 pp. 325-332.
Balzano, G. et al; "Effectiveness and Acceptability of a Domiciliary Multidrug Inhalation Treatment in Elderly Patients with Chronic Airflow Obstruction: Metered Dose Inhaler Versus Jet Nebulizer"; J. of Aerosol Medicine (2000) vol. 13, No. 1, 2000, pp. 25-33.
Bedi, Rajinder Singh; Inhaled Corticosteroids in COPD; Indian Journal Chest Dis Allied Sci (2005) vol. 47, pp. 243-244.

(Continued)

*Primary Examiner* — Brian McDowell
(74) *Attorney, Agent, or Firm* — Michael P. Morris; Edouard G. Lebel

(57) ABSTRACT

The present invention relates to a process for preparing betamimetics of formula 1,

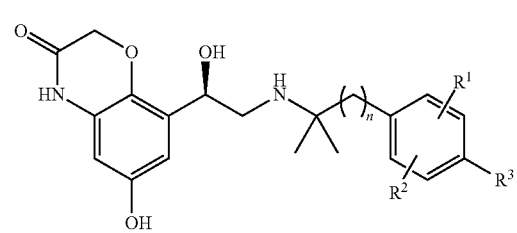

wherein
n denotes 1 or 2;
$R^1$ denotes hydrogen, halogen, $C_{1-4}$-alkyl or $O$—$C_{1-4}$-alkyl;
$R^2$ denotes hydrogen, halogen, $C_{1-4}$-alkyl or $O$—$C_{1-4}$-alkyl;
$R^3$ denotes hydrogen, $C_{1-4}$-alkyl, OH, halogen, $O$—$C_{1-4}$-alkyl, $O$—$C_{1-4}$-alkylene-COOH, $O$—$C_{1-4}$-alkylene-COO—$C_{1-4}$-alkyl.

5 Claims, No Drawings

U.S. PATENT DOCUMENTS

| | | |
|---|---|---|
| 7,727,984 B2 | 6/2010 | Konetzki et al. |
| 7,786,111 B2 | 8/2010 | Konetzki et al. |
| 8,034,809 B2 | 10/2011 | Lustenberger et al. |
| 8,044,046 B2 | 10/2011 | Konetzki et al. |
| 2001/0008632 A1 | 7/2001 | Freund et al. |
| 2002/0002262 A1 | 1/2002 | Bier |
| 2002/0022625 A1 | 2/2002 | Walland et al. |
| 2002/0091115 A1 | 7/2002 | Dyatkin et al. |
| 2002/0115680 A1 | 8/2002 | Meissner et al. |
| 2002/0119991 A1 | 8/2002 | Meissner et al. |
| 2002/0189610 A1 | 12/2002 | Bozung et al. |
| 2003/0018019 A1 | 1/2003 | Meade et al. |
| 2003/0043687 A1 | 3/2003 | Boeck et al. |
| 2003/0119859 A1 | 6/2003 | Gavin |
| 2003/0152523 A1 | 8/2003 | Martin et al. |
| 2003/0207912 A1 | 11/2003 | Eickmeier et al. |
| 2004/0002502 A1 | 1/2004 | Banholzer et al. |
| 2004/0010003 A1 | 1/2004 | Banholzer et al. |
| 2004/0024007 A1 | 2/2004 | Pairet et al. |
| 2004/0044020 A1 | 3/2004 | Meade et al. |
| 2004/0048886 A1 | 3/2004 | Meade et al. |
| 2004/0048887 A1 | 3/2004 | Meade et al. |
| 2004/0058950 A1 | 3/2004 | Meade et al. |
| 2004/0087617 A1 | 5/2004 | Meissner et al. |
| 2004/0121996 A1 | 6/2004 | Barvian et al. |
| 2004/0122108 A1 | 6/2004 | Buettner et al. |
| 2004/0132759 A1 | 7/2004 | Konetzki et al. |
| 2004/0138307 A1 | 7/2004 | Konetzki et al. |
| 2004/0147513 A1 | 7/2004 | Konetzki et al. |
| 2004/0166065 A1 | 8/2004 | Schmidt |
| 2004/0228805 A1 | 11/2004 | Pieper et al. |
| 2005/0004228 A1 | 1/2005 | Konetzki |
| 2005/0008578 A1 | 1/2005 | Schmidt |
| 2005/0025718 A1 | 2/2005 | Meade et al. |
| 2005/0026948 A1 | 2/2005 | Meade et al. |
| 2005/0101625 A1 | 5/2005 | Boeck et al. |
| 2005/0137242 A1 | 6/2005 | Walland et al. |
| 2005/0154006 A1 | 7/2005 | Meade et al. |
| 2005/0165013 A1 | 7/2005 | Meade et al. |
| 2005/0186175 A1 | 8/2005 | Meade et al. |
| 2005/0222144 A1 | 10/2005 | Konetzki et al. |
| 2005/0239778 A1 | 10/2005 | Konetzki et al. |
| 2005/0255050 A1 | 11/2005 | Trunk et al. |
| 2005/0256114 A1 | 11/2005 | Grauert et al. |
| 2005/0256115 A1 | 11/2005 | Aven |
| 2005/0267106 A1 | 12/2005 | Lustenberger et al. |
| 2005/0272726 A1 | 12/2005 | Konetzki et al. |
| 2006/0003268 A1 | 1/2006 | Hong et al. |
| 2006/0057074 A1 | 3/2006 | Meade et al. |
| 2006/0063817 A1 | 3/2006 | Bouyssou et al. |
| 2006/0106213 A1 | 5/2006 | Konetzki et al. |
| 2006/0116398 A1 | 6/2006 | Mammen et al. |
| 2006/0189607 A1 | 8/2006 | Konetzki et al. |
| 2006/0222598 A1 | 10/2006 | Schmidt |
| 2007/0027148 A1 | 2/2007 | Lustenberger et al. |
| 2007/0066609 A1 | 3/2007 | Bouyssou et al. |
| 2007/0086957 A1 | 4/2007 | Bouyssou et al. |
| 2007/0088030 A1 | 4/2007 | Niklaus-Humke et al. |
| 2007/0088160 A1 | 4/2007 | Krueger et al. |
| 2007/0148598 A1 | 6/2007 | Colburn et al. |
| 2007/0155741 A1 | 7/2007 | Konetzki et al. |
| 2008/0041369 A1 | 2/2008 | Radau et al. |
| 2008/0041370 A1 | 2/2008 | Radau et al. |
| 2008/0063608 A1 | 3/2008 | Pieper et al. |
| 2008/0167298 A1 | 7/2008 | Konetzki et al. |
| 2008/0280897 A1 | 11/2008 | Aven |
| 2008/0293710 A1 | 11/2008 | Aven |
| 2009/0088408 A1 | 4/2009 | Meade et al. |
| 2009/0092558 A1 | 4/2009 | Konetzki et al. |
| 2009/0099225 A1 | 4/2009 | Freund et al. |
| 2009/0137578 A1 | 5/2009 | Lustenberger et al. |
| 2009/0155185 A1 | 6/2009 | Meade et al. |
| 2009/0181961 A1 | 7/2009 | Konetzki et al. |
| 2009/0185983 A1 | 7/2009 | Freund et al. |
| 2010/0009984 A1 | 1/2010 | Niklaus-Humke et al. |
| 2010/0022770 A1 | 1/2010 | Rodriguez Dehli et al. |
| 2010/0331288 A1 | 12/2010 | Aven et al. |
| 2011/0135582 A1 | 6/2011 | Bouyssou et al. |
| 2011/0190284 A1 | 8/2011 | Niklaus-Humke et al. |
| 2011/0281858 A1 | 11/2011 | Aven |
| 2011/0319402 A1 | 12/2011 | Heblich |
| 2012/0034275 A1 | 2/2012 | Trunk et al. |
| 2012/0035169 A1 | 2/2012 | Aven |
| 2012/0058980 A1 | 3/2012 | Radau et al. |
| 2012/0263655 A1 | 10/2012 | Bouyssou et al. |

FOREIGN PATENT DOCUMENTS

| | | |
|---|---|---|
| CA | 2225601 A1 | 1/1997 |
| CA | 2232151 A1 | 4/1997 |
| CA | 2233981 C | 4/1997 |
| CA | 2237853 C | 6/1997 |
| CA | 2275392 A1 | 7/1998 |
| CA | 2300908 A1 | 4/1999 |
| CA | 2405745 A1 | 11/2001 |
| CA | 2450961 A1 | 1/2003 |
| CA | 2455167 A1 | 1/2003 |
| CA | 2454935 A1 | 2/2003 |
| CA | 2425539 A1 | 4/2003 |
| CA | 2425557 A1 | 4/2003 |
| CA | 2471578 A1 | 8/2003 |
| CA | 2479652 A1 | 9/2003 |
| CA | 2481876 A1 | 10/2003 |
| CA | 2492037 A1 | 1/2004 |
| CA | 2495454 A1 | 3/2004 |
| CA | 2501055 A1 | 4/2004 |
| CA | 2506082 A1 | 6/2004 |
| CA | 2506109 A1 | 6/2004 |
| CA | 2558067 A1 | 10/2005 |
| CA | 2559699 A1 | 11/2005 |
| CA | 2559700 A1 | 11/2005 |
| CA | 2562859 A1 | 11/2005 |
| CA | 2564379 A1 | 11/2005 |
| CA | 2565915 A1 | 11/2005 |
| CA | 2624584 A1 | 4/2007 |
| CA | 2624786 A1 | 4/2007 |
| CA | 2660480 A1 | 2/2008 |
| CA | 2660488 A1 | 2/2008 |
| CA | 2675094 A1 | 7/2008 |
| CA | 2738616 A1 | 5/2010 |
| CA | 2738617 A1 | 5/2011 |
| DE | 1144713 A1 | 3/1963 |
| DE | 3625685 A1 | 3/1987 |
| DE | 102004019540 A1 | 11/2005 |
| DE | 102004024454 A1 | 12/2005 |
| EP | 0072505 A1 | 3/1983 |
| EP | 0073505 A1 | 3/1983 |
| EP | 0237507 A1 | 9/1987 |
| EP | 0321864 A2 | 6/1989 |
| GB | 2106102 A | 4/1983 |
| JP | 09-012518 A | 1/1997 |
| JP | 11-255743 A | 9/1999 |
| WO | 91/14468 A1 | 10/1991 |
| WO | 94/07607 A1 | 4/1994 |
| WO | 94/28958 A1 | 12/1994 |
| WO | 9701329 A1 | 1/1997 |
| WO | 97/12683 A1 | 4/1997 |
| WO | 97/12687 A1 | 4/1997 |
| WO | 97/20590 A1 | 6/1997 |
| WO | 9827959 A2 | 7/1998 |
| WO | 99/16530 A1 | 4/1999 |
| WO | 01/58425 A2 | 8/2001 |
| WO | 01/83462 A1 | 11/2001 |
| WO | 02/30928 A1 | 4/2002 |
| WO | 02/32899 A1 | 4/2002 |
| WO | 02080884 A2 | 10/2002 |
| WO | 03/000241 A2 | 1/2003 |
| WO | 03/000265 A1 | 1/2003 |
| WO | 03011810 A1 | 2/2003 |
| WO | 03017970 A1 | 3/2003 |
| WO | 03/064417 A1 | 8/2003 |
| WO | 03/078429 A1 | 9/2003 |
| WO | 03/084502 A1 | 10/2003 |
| WO | 2004000840 A2 | 12/2003 |
| WO | 2004004775 A1 | 1/2004 |
| WO | 2004022058 A1 | 3/2004 |
| WO | 2004033412 A1 | 4/2004 |
| WO | 2004/045618 A2 | 6/2004 |

| | | | |
|---|---|---|---|
| WO | 2004046083 A1 | 6/2004 |
| WO | 2004/087142 A | 10/2004 |
| WO | 2005014044 A1 | 2/2005 |
| WO | 2005092870 A1 | 10/2005 |
| WO | 2005/102349 A1 | 11/2005 |
| WO | 2005/111005 A1 | 11/2005 |
| WO | 2005102350 A1 | 11/2005 |
| WO | 2005110359 A1 | 11/2005 |
| WO | 2005110421 A1 | 11/2005 |
| WO | 2007/020227 A1 | 2/2007 |
| WO | 2007042153 | 4/2007 |
| WO | 2007042467 A1 | 4/2007 |
| WO | 2007042468 A2 | 4/2007 |
| WO | 2007054498 A1 | 5/2007 |
| WO | 2007148806 A1 | 12/2007 |
| WO | 2008020056 A2 | 2/2008 |
| WO | 2008020057 A1 | 2/2008 |
| WO | 2008024045 A1 | 2/2008 |
| WO | 2008090193 A2 | 7/2008 |
| WO | 2009059893 A1 | 5/2009 |
| WO | 2010057927 A1 | 5/2010 |
| WO | 2010057928 A1 | 5/2010 |

OTHER PUBLICATIONS

Bernstein, J; Controlling the Polymorphic Form Obtained; Polymorphism in Molecular Crystals in Chapter 3; Clarendon Press, Oxford, 2002, pp. 66-93.

Bernstein, J; Analytical Techniques for Studying and Characterizing Polymorphs; Analytical Techniques for Studying and Characterizing Polymorphs; Polymorphism in Molecular Crystals in Chapter 4; Clarendon Press, Oxford, 2002, pp. 94-150.

Brittain, Harry G., et al; Physical Characterization of Pharmaceutical Solids; Pharmaceutical Research (1991) vol. 8, pp. 963-973.

Brittain, Harry G., et al; Overview of Physical Characterization Methodology; Physical Characterization of Pharmaceutical Solids in Chapter 1; Marcel Dekker, New York, 1995, pp. 1-35.

Brittain, Harry G; Methods for the Characterization of Polymorphs and Solvates in Chapter 6; Polymorphism in Pharmaceutical Solids; Marcel Dekker, New York, 1999, pp. 227-278.

Brittain, Harry G; Solid State Analysis; Handbook of Modern Pharmaceutical Analysis in Chapter 3; Marcel Dekker, New York, 2001, pp. 57-84.

Brittain, Harry G; Preparation and identification of Polymorphs and Solvatomorphs; Preformulation in Solid Dosage Form Development; Informa Healthcare Press, New York, 2008, pp. 185-228.

Bugay, David E; Characterization of the Solid-State: Spectroscopic Techniques; Advanced Drug Delivery Reviews (2001) vol. 48, pp. 43-65.

Buu-Hoi, N. P. et al; Alpha, Alpha-Dimethyl-Beta-Arylethymanines, and Their Behavior in the Bischler-Napieralski Reaction; Journal of Organic Chemistry (1958) vol. 23, No. 1 pp. 42-45.

Chronic Obstructive Pulmonary Disease (Wikepedia) Jul. 3, 2008.

Crapo, James D., et al; Beta-Adrenergic Receptor Agonists; Baum's Textbook of Pulmonary Disease; 7$^{th}$ Edition (2004) Lippincott Williams & Wilkins.

Declaration of Dr. Andreas Schnapp Under 37 C.F.R. § 1.132 submitted in U.S. Appl. No. 11/109,030, filed Apr. 19, 2005.

Dutu, S. et al; Lung Function in COPD Patients Under Long Term Inhaled Therapy With Bronchodilator Agents and Beclometasone, European Respiratory Journal, (1997) Supp., Bd. 10, Nr. 25, Supp. 20.

Gavezzotti, "Are Crystal Structures Predictable?" Accounts of Chemical Research, vol. 27, pp. 309-314 (1994).

GINA: Global Initiative for Asthma: Pocket Guide for Asthma Management and Prevention (2005) 30 pages.

Griesser, Ulrich J.; The Importance of Solvates; Polymorphism: in the Pharmaceutical Industry (2006) chapter 8; pp. 211-233.

Guillory, J, Keith; Generation of Polymorphs, Hydrates, Solvated, and Amorphous Solids; Marcel Dekker, New York, 1999, pp. 183-226.

Hamada, Takayuki et al; Practical Synthesis of Optically Active Styrene Oxides Via reductive Transformation of 2-Chloroacetophenones with Chiral Rhodium Catalysts; Organic Letters (2002) vol. 4 No. 24 pp. 4373-4376.

Hilfiker, Rolf et al; Polymorphism—Integrated Approach from High-Throughput Screening to Crystallization Optimization; Journal of Thermal Analysis and Calorimetry (2003) vol. 73, pp. 429-440.

Hilfiker, Rolf et al; Approaches to Polymorphism Screening; Polymorphism in the Pharmaceutical Industry in Chapter 11; Wiley-VCH, Mannheim, 2006, pp. 287-308.

Jackson, Catherine M. et al; Benefit-Risk Assessment of Long-Acting B2-Agonists in Asthma; Drug Safety 2004 vol. 27 No. 4 pp. 243-270.

Klimanskaya, E.V.; Chronic Obstructive Lung Diseases in Children; http://www.nedug.ru/lib/lit/therap/01oct/therap204/therap.htm (2008) pp. 1-5.

Martinez, Fernando J. et al; Is It Astham or COPD? Postgraduate Medicine Online (2005) vol. 117, No. 3, pp. 1-13.

Merck Manual Home Edition; Respiratory Distress Syndrome; Acidosis; Pneumococcal Infections; Lung Cancer and Severe Acute Respiratory Syndrome (SARS); retrieved Jun. 10, 2007.

Morissette, Sherry L., et al; High-Throughput Crystallization: Polymorphs, Salts, Co-Crystals and Solvates of Pharmaceutical Solids; Advanced Drug Delivery Reviews (2004) vol. 56, pp. 275-300.

Newman, Ann W., et al; Form Selection of Pharmaceutical Compounds; Handbook of Pharmaceutical Analysis in Chapter 1; Marcel Dekker; New York, 2001, pp. 1-57.

O'Byrne, Paul M. et al; Inhaled Beta 2-Agonists in the Treatment of Asthma; The New England Journal of Medicine (1996) vol. 335 No. 12 pp. 886-888.

Sovani, Milind P. et al; A Benefit-Risk Assessment of Inhaled Long-Acting B2-Agonists in the Management of Obstructive Pulmonary Disease; Drug Safety 2004 vol. 27 No. 10 pp. 689-715.

Storey, PD.D, Richard A., et al; Integration of High Throughput Screening Methodologies and Manual Processes for Solid Form Selection; American Pharmaceutical Review (2003) pp. 100-105.

Threlfall, Terence L; Analysis of Organic Polymorphs: A Review; Analyst (1995) vol. 120, pp. 2435-2460.

Timberlake, Jack W. et al; Thiadiaziridine 1,1-Dioxides: Synthesis and Chemistry; Journal of Organic Chemistry (1981) vol. 46, No. 10 pp. 2082-2089; American Chemical Society.

Ukena, D.; Ciclesonide—A New Inhaled Corticosteroid. Pharmacological Properties and Clinical Efficacy in the Treatment of Asthma; Pneumalogie (2005) vol. 59 pp. 689-695.

Waldeck, Bertil; Beta-Adrenoceptor Agonists and Asthma—100 Years of Development; European Journal of Pharmacology (2002) vol. 445 pp. 1-12.

www.betterhealthcenter.com/allergy-asthma.htm: pp. 1 or 4 and 2 of 4; retrieved Mar. 26, 2006.

Yasuda, Masahide et al; Redox-Photosensitized Aminations of 1,2-Benso-1,3-Cycloalkadienes, Arylcyclopropanes, and Quadricyclane with Ammonia; Journal of Organic Chemistry (2003) vol. 68, No. 20 pp. 7618-7624; American Chemistry Society.

Vippagunta, Sudha R. et al; Crystalline Solids; Advanced Delivery Reviews (2001) vol. 48, pp. 3-26.

International Search Report for PCT/EP03/12565 mailed on Aug. 4, 2004.

International Search Report for PCT/EP2005/004073 mailed on Aug. 3, 2005.

International Search Report for PCT/EP2005/004075 mailed on Aug. 3, 2005.

International Search Report for PCT/EP2005/005028 mailed on Jan. 24, 2006.

International Search Report for PCT/EP2005/005078 mailed on Oct. 28, 2005.

International Search Report for PCT/EP2005/005079 mailed on Aug. 8, 2005.

International Search Report for PCT/EP2006/067126 mailed on Jun. 4, 2007.

International Search Report PCT/EP2006/065217 mailed on Nov. 22, 2006.

International Search Report PCT/EP2006/067122 mailed on Feb. 12, 2007.

International Patent Application PCT/EP2008/064201 filed under the PCT on Oct. 21, 2008.

Non-Final Office Action dated Feb. 25, 2005 from U.S. Appl. No. 10/705,012, filed Nov. 10, 2003.

Non-Final Office Action dated Jun. 21, 2005 from U.S. Appl. No. 10/705,012, filed Nov. 10, 2003.
Notice of Allowability dated Dec. 12, 2005 from U.S. Appl. No. 10/705,012, filed Nov. 10, 2003, now U.S. Patent No. 7,056,816.
Final Office Action dated Mar. 8, 2007 from U.S. Appl. No. 11/109,030, filed Apr. 19, 2005.
Non-Final Office Action dated Nov. 29, 2007 from U.S. Appl. No. 11/109,030, filed Apr. 19, 2005.
Non-Final Office Action dated Sep. 22, 2008 from U.S. Appl. No. 11/109,030, filed Apr. 19, 2005.
Office Action dated Apr. 18, 2007 from U.S. Appl. No. 11/125,756, filed May 10, 2005.
Final Office Action dated Dec. 18, 2007 from U.S. Appl. No. 11/125,756, filed May 10, 2005.
Non-Final Office Action dated Sep. 28, 2006 from U.S. Appl. No. 11/125,890, filed May 10, 2005.
Final Office Action dated Mar. 1, 2007 from U.S. Appl. No. 11/125,890, filed May 10, 2005.
Non-Final Office Action dated Dec. 28, 2005 from U.S. Appl. No. 11/128,032, filed May 12, 2005.
Non-Final Office Action dated Nov. 21, 2006 from U.S. Appl. No. 11/128,032, filed May 12, 2005.
Office Action dated Jun. 14, 2007 from U.S. Appl. No. 11/128,141, filed May 12, 2005.
Response to Office Action dated Dec. 12, 2007 from U.S. Appl. No. 11/128,141, filed May 12, 2005.
Response to Office Action filed Dec. 12, 2007 from U.S. Appl. No. 11/128,141, filed May 12, 2005.
Non-Final Office Action dated Mar. 24, 2008 from U.S. Appl. No. 11/128,141, filed May 12, 2005.
Office Action dated Apr. 25, 2008 from U.S. Appl. No. 11/132,075, filed May 18, 2005.
Non-Final Office Action dated Jul. 17, 2007 from U.S. Appl. No. 11/222,149, filed Sep. 8, 2005.
Non-Final Office Action dated Mar. 20, 2006 from U.S. Appl. No. 11/275,730, filed Jan. 26, 2006.
Final Office Action dated Oct. 23, 2006 from U.S. Appl. No. 11/275,730, filed Jan. 26, 2006.
Non-Final Office Action dated Mar. 28, 2008 from U.S. Appl. No. 11/543,168, filed Oct. 4, 2006.
Non-Final Office Action dated Apr. 4, 2008 U.S. Appl. No. 11/543,477, filed Oct. 5, 2006.
Non-Final Office Action dated Apr. 3, 2008 U.S. Appl. No. 11/543,694, filed Oct. 5, 2006.
Non-Final Office Action dated Jun. 4, 2007 from U.S. Appl. No. 11/600,417, filed Nov. 15, 2006.
Office Action dated May 24, 2007 from U.S. Appl. No. 11/677,112, filed Feb. 21, 2007.
Non-Final Office Action dated Apr. 30, 2008 from U.S. Appl. No. 11/677,112, filed Feb. 21, 2007.
Office Action dated Apr. 28, 2008 from U.S. Appl. No. 12/036,618, filed Feb. 25, 2008.
Non-Final Office Action dated Jan. 3, 2006 from U.S. Patent No. 7,160,882 B2.
Non-Final Office Action dated Jun. 5, 2006 from U.S. Patent No. 7,160,882 B2.
U.S. Appl. No. 11/676,823, filed Feb. 20, 2007.
U.S. Appl. No. 12/093,026, filed May 8, 2008.
U.S. Appl. No. 12/036,618, filed Feb. 25, 2008.
U.S. Appl. No. 12/133,066, filed Jun. 4, 2008.
Bouyssou, T. et al. "Discovery of Olodaterol, a Novel Inhaled β2-Adrenoceptor Agonist with a 24 h Bronchodilatory Efficacy" Bioorganic & Medicinal Chemistry Letters, 20, (2010) pp. 1410-1414.
Bouyssou, T. et al. "Pharmacological Characterization of Olodaterol, a Novel Inhaled β2-Adrenoceptor Agonist Exerting a 24-Flour-Long Duration of Action in Preclinical Models" The Journal of Pharmacology and Experimental Therapeutics, vol. 334 No. 1, (2010) pp. 53-62.
Braga, et al. "Making crystals from crystals: a green route to crystal engineering and polymorphism" ChemComm 2005, 3635-3645.
Buettner, F. et al. "Betamimetics with a prolonged duration of activity, processes for preparing them, and their use as pharmaceutical compositions"; U.S. Appl. No. 10/666,068, filed Sep. 19, 2003.
Calvo, G. Mario; Is it useful to add an Anticholinergic Treatment to b2-Adrenergic Medication in Acute Asthma Attach? Invest. Allegorl Clin Immunol (1998) V 8, No. 1 pp. 30-34.
Coutts, Ronald T. et al; Synthesis of Two in Vivo Metabolites of N-(N-Propyl)Phentermine; Canadian Journal of Chemistry (1978) vol. 56 pp. 3054-3058.
Decision from the Board of Patent Appeals and Interferences in Appeal No: 2000-0600. (May 6, 2002).
Declaration of Dr. Harry G. Brittain under 37 C.F.R. x 1.132 submitted in U.S. Appl. No. 11/677,112 on Apr. 1, 20009 and U.S. Appl. No. 11/132,075 on Apr. 3, 2009.
Derwent Publications Ltd. GB, Class B05, Nov. 10, 1998.
EP 05292120.2 US PTO Oct 11, 2005.
Final Office Action dated Jun. 28, 2011 in U.S. Appl. No. 11/109,094, filed Apr. 19, 2005.
Final Office Action dated Mar. 11, 2011 from U.S. Appl. No. 12/407,982, filed Mar. 20, 2009.
GOLD Pocket Guide, Jul. 2003.
GOLD Pocket Guide, Jul. 2004.
International Preliminary Report on Patentability for PCT/EP2007/058518 filed Aug. 16, 2007 and issued Mar. 17, 2009.
International Preliminary Report on Patentability for PCT/EP2007/058518 filed Aug. 16, 2007 and issued Mar. 17, 2009. (English Translation).
International Search Report for PCT/EP2007/058518 filed Aug. 16, 2007 and mailed Oct. 19, 2007.
International Search Report for PCT/EP2009/065406 mailed on Jan. 12, 2010.
International Search Report for PCT/EP2009/065407 mailed on Jan. 20, 2010.
International Search Report PCT/EP2006/068191 mailed Feb. 5, 2007.
International Search Report PCT/EP2008/050800 mailed Aug. 13, 2009.
Lovoilette, et al. "Montelukast Added to Inhaled Beclomethasone in Treatment of Asthma" Am J Respir Crit Care Med 1999, 160:1862-1868.
Nicholson, et al. "Involvement of steroid hormone and growth factor cross-talk in endocrine response in breast cancer" Endocrine-Related Cancer (1999) 6 373-387.
Non-Final Office Action dated Dec. 8, 2010 from U.S. Appl. No. 11/128,141, filed May 12, 2005.
Non-Final Office Action dated Mar. 16, 2011 from U.S. Appl. No. 12/133,066, filed Jun. 4, 2008.
Office Action dated Mar. 18, 2011, in U.S. Appl. No. 12/093,026, filed Jul. 14, 2008.
Schwender, Charles F. et al. "3[a-(tert-Butylamino)methyl]-5-hydroxy-m-xylene-a,a'-diol, a Selective Bronchodilator" Journal of Medicinal Chemistry, (1974) vol. 17, No. 10, pp. 1112-1115.
Seddon, et al. "Pseudopolymorph: A Polemic" American Chemical Society (2004).
Sereda, V.P., et al; Inhalation Therapy of Chronic Obstructive Lung Diseases; www.pharmindex.ru/practic/4_pulmo.html <http://www.pharmindex.ru/practic/4_pulmo.html>. Feb. 2003, pp. 1-35.
Tamura, Yasumitsu et al. "erythro-5[1-Hydroxy-2-(isopropylamino)butyl]-7-hydroxycarbostyril, a Terbutaline-Type Derivative of the Bronchodilator Procaterol" J. Med. Chem. (1981) vol. 24, pp. 634-636.
U.S. Appl. No. 13/332,984, filed Dec. 21 2011, Ingo Konetzki.
West, Anthony R., "Solid State Chemistry and its Applications" Wiley, New York 1988 pp. 358-365.
Wolf, Manfred E; Burger's Medicinal Chemistry, 5ed, Part 1, John Wiley & Sons, (1995) pp. 975-977.
Written Opinion of ISA for PCT/EP2009/065406 mailed on Jan. 12, 2010.
Written Opinion of ISA for PCT/EP2009/065407 mailed on Jan. 20, 2010.
Gould, Philip L. "Salt selection for basic drugs" International Journal of Pharmaceutics (1986) 33, pp. 201-217.

PROCESS FOR THE MANUFACTURING OF BETAMIMETICS

This application is a continuation application of U.S. application Ser. No. 11/463,703, filed Aug. 10, 2006, now abandoned, which claims the benefit of European Patent Application EP 05107470, filed Aug. 15, 2005, the contents of which are incorporated herein in their entireties.

The present invention relates to a process for preparing betamimetics of formula 1,

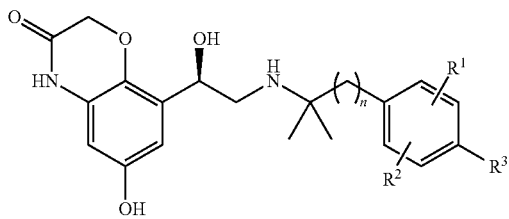

wherein
n denotes 1 or 2;
R¹ denotes hydrogen, halogen, C₁₋₄-alkyl or O—C₁₋₄-alkyl;
R² denotes hydrogen, halogen, C₁₋₄-alkyl or O—C₁₋₄-alkyl;
R³ denotes hydrogen, C₁₋₄-alkyl, OH, halogen, O—C₁₋₄-alkyl, O—C₁₋₄-alkylene-COOH, O—C₁₋₄-alkylene-COO—C₁₋₄-alkyl.

BACKGROUND TO THE INVENTION

Betamimetics (β-adrenergic substances) are known from the prior art. For example reference may be made in this respect to the disclosure of U.S. Pat. No. 4,460,581, which proposes betamimetics for the treatment of a range of diseases.

For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree. It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide a method of producing betamimetics which on the one hand confer a therapeutic benefit in the treatment of COPD or asthma and are also characterised by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day for treating COPD or asthma. A further objective of the invention, apart from those mentioned above, is to prepare betamimetics which are not only exceptionally potent but are also characterised by a high degree of selectivity with respect to the β₂-adrenoceptor.

DETAILED DESCRIPTION OF THE INVENTION

The present invention relates to a process for preparing a compound of formula 1,

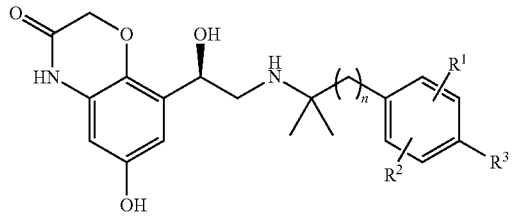

wherein
n denotes 1 or 2;
R¹ denotes hydrogen, halogen, C₁₋₄-alkyl or O—C₁₋₄-alkyl;
R² denotes hydrogen, halogen, C₁₋₄-alkyl or O—C₁₋₄-alkyl;
R³ denotes hydrogen, C₁₋₄-alkyl, OH, halogen, O—C₁₋₄-alkyl, O—C₁₋₄-alkylene-COOH, O—C₁₋₄-alkylene-COO—C₁₋₄-alkyl,
characterised in that a compound of formula 1a,

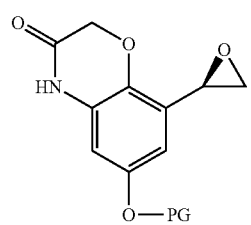

wherein PG represents a protective group, is reacted with a compound of formula 1b,

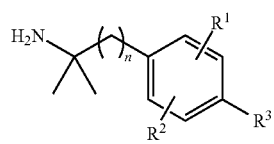

wherein R¹, R², R³ and n have the meaning given above, in an organic solvent to yield a compound of formula 1c,

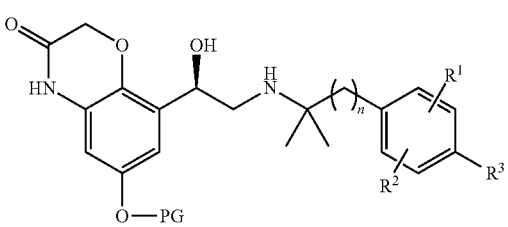

wherein R¹, R², R³, n and PG have the meanings given above, and the compound of formula 1 is obtained therefrom by cleaving the protective group PG.

The above process is preferably used to prepare compounds of formula 1, wherein
n denotes 1 or 2;
R¹ denotes hydrogen, halogen or C₁₋₄-alkyl;
R² denotes hydrogen, halogen or C₁₋₄-alkyl;
R³ denotes hydrogen, C₁₋₄-alkyl, OH, halogen, O—C₁₋₄-alkyl, O—C₁₋₄-alkylene-COOH or O—C₁₋₄-alkylene-COO—C₁₋₄-alkyl.

The above process is preferably used to prepare compounds of formula 1, wherein
n denotes 1 or 2;
R¹ denotes hydrogen, fluorine, chlorine, methyl or ethyl;
R² denotes hydrogen, fluorine, chlorine, methyl or ethyl;
R³ denotes hydrogen, C$_{1-4}$-alkyl, OH, fluorine, chlorine, bromine, O—C$_{1-4}$-alkyl, O—C$_{1-4}$-alkylene-COOH, O—C$_{1-4}$-alkylene-COO—C$_{1-4}$-alkyl.

The above process is preferably used to prepare compounds of formula 1, wherein
n denotes 1 or 2;
R¹ denotes hydrogen, methyl or ethyl;
R² denotes hydrogen, methyl or ethyl;
R³ denotes hydrogen, methyl, ethyl, OH, methoxy, ethoxy, O—CH$_2$—COOH, O—CH$_2$—COO-methyl or O—CH$_2$—COO-ethyl.

The above process is preferably used to prepare compounds of formula 1, wherein
n denotes 1 or 2;
R¹ denotes hydrogen or methyl;
R² denotes hydrogen or methyl;
R³ denotes hydrogen, methyl, OH, methoxy, O—CH$_2$—COOH or O—CH$_2$—COO-ethyl.

In the process according to the invention a compound of formula 1a is reacted with a compound of formula 1b in a suitable solvent. Suitable solvents which may be used are organic solvents, while particularly preferred solvents are selected from among tetrahydro-furan, toluene, ethanol, n-propanol, n-butanol, n-butylacetate, dimethylformamide, methoxyethanol, ethyleneglycol and dioxane. According to the invention particularly preferred solvents are n-propanol, tetrahydrofuran and dioxane, while dioxane and n-propanol are of particular importance.

Based on the compound 1a used it is preferable according to the invention to use at least stoichiometric amounts of compound 1b. Compound 1b may optionally also be used in excess, for example in amounts of up to 3 equivalents, preferably up to 2.5 equivalents, particularly preferably about 1 to 2, optionally 1 to 1.5 equivalents based on the compound 1a used.

The reaction is preferably carried out at elevated temperature, preferably at a temperature above 40° C., particularly preferably at a temperature above 50° C. Particularly preferably, the reaction mixture is heated to the boiling temperature of the solvent used.

At this temperature the reaction is then carried out over a period of about 1 to 72 hours, preferably 10 to 60 hours, particularly preferably 20 to 50 hours.

Once the reaction has ended the solvent is eliminated and the residue remaining is taken up in an organic polar solvent, preferably a C$_{1-8}$-alcohol or C$_{3-8}$-ester, particularly preferably in ethanol or ethyl acetate, and filtered. The filtrate is acidified, preferably with an inorganic acid, particularly preferably with hydrochloric acid and after a period of about 10 minutes to 12 hours, preferably 20 minutes to 6 hours, particularly preferably 30 minutes to 3 hours, the product is filtered off.

The protective group PG is preferably cleaved from compounds of formula 1a by hydrogenation in a suitable solvent. Examples of suitable solvents include organic solvents, preferably organic, polar solvents, particularly preferred solvents are selected from among tetrahydrofuran, various C$_{3-8}$-esters and C$_{1-8}$-alcohols. Preferably, according to the invention, the solvents used are tetrahydrofuran, ethanol and methanol, while ethanol and methanol are of particular significance.

The hydrogenation in the process according to the invention preferably uses catalysts in the presence of hydrogen. Preferred catalysts are suitable transition metal catalysts, preferably heterogeneous transition metal catalysts, particularly preferably palladium-containing catalysts, particularly a palladium-charcoal mixture.

The hydrogenation is preferably carried out in the presence of an excess of hydrogen. The latter is provided according to the invention by a hydrogen pressure of 1 bar to 10 bar, preferably between 2 and 7 bar, particularly preferably between 2.5 and 4.5 bar.

Preferably the hydrogenation is carried out at elevated temperature, preferably from 25 to 70° C., particularly preferably from 30 to 60° C., particularly from 35 to 50° C. After the reaction has ended the catalyst is removed, preferably by filtration.

Then the solvent is eliminated and the product is recrystallised from a suitable organic solvent, preferably a C$_{1-8}$-alcohol or a mixture of C$_{1-8}$-alcohols, particularly preferably from a mixture of methanol and an alcohol selected from among i-propanol, n-propanol and ethanol.

In a preferred process according to the invention the compound of formula 1a is prepared by reacting a compound of formula 2a,

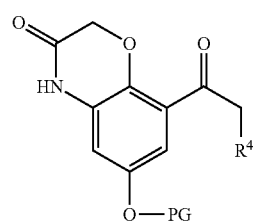

2a wherein PG has the meaning given in claim 1 and R⁴ denotes halogen, preferably bromine or chlorine.

In the process according to the invention a compound of formula 2a is reacted in a suitable solvent with DIP chloride (diisopinocampheylchloroborane). Suitable solvents are preferably organic solvents. Preferred solvents are selected from among diethyl ether, tert-butyl-methylether 2-methyltetrahydrofuran, tetrahydrofuran, toluene and dioxane. Particularly preferably according to the invention the solvents used are tert-butyl-methylether, tetrahydrofuran and dioxane, of which dioxane and tetrahydrofuran are of particular importance.

The DIP chloride may be used in pure form or in the form of a solution, preferably in an inert organic solvent, particularly preferably an aliphatic solvent, particularly pentane, hexane, heptane or octane.

The DIP chloride is added at reduced temperature in the reaction medium, the temperature preferably being below 0° C., particularly preferably below −10° C.; more particularly the addition is carried out at −20 to −40° C.

The DIP chloride is added over a period of 10 min to 6 hours, preferably 30 min to 4 hours, particularly preferably 1 to 3 hours. In particular, the addition takes place over a period of 70 to 110 min.

Based on the compound 2a used, according to the invention at least stoichiometric amounts of DIP chloride are preferably used. The DIP chloride may optionally also be used in excess, for example in amounts of up to 3 equivalents, preferably 2.5 equivalents, particularly preferably 1.5 to 2.5 equivalents based on the compound 2a used.

After the DIP chloride has been added the reaction mixture is stirred over a period of 10 min to 4 hours, preferably 30 min to 3 hours, particularly preferably 40 to 80 min; in particular, the reaction mixture is stirred for another 50 to 70 min after the addition has ended. During this time the reaction mixture is adjusted to a temperature of −20 to 20° C., particularly preferably from −10 to 10° C., particularly from −5 to 5° C.

Once the desired temperature has been reached, an at least stoichiometric amount of sodium hydroxide (NaOH), dissolved in water, is added, based on the amount of DIP chloride used. If desired the NaOH may also be used in excess, for example in amounts of up to 3 equivalents, preferably in amounts of up to 2.5 equivalents, particularly preferably 1.5 to 2.5 equivalents, based on the amount of DIP chloride used. Preferably a pH value of 12 to 14, particularly preferably 12.5 to 13.5, particularly 12.7 to 13.3 is measured in the reaction mixture after the addition of NaOH has ended.

After the desired pH has been selected, the reaction mixture is stirred over a period of 10 min to 4 hours, preferably 30 min to 3 hours, particularly preferably 40-80 min, and in particular the reaction mixture is stirred for a further 50-70 min During this time the reaction mixture is adjusted to a temperature of 0 to 40° C., particularly preferably from 10 to 30° C., particularly from 15 to 25° C. Then the reaction mixture is adjusted to a pH of 7 to 10, particularly preferably 8 to 9, particularly 8.2 to 8.8, with an acid, preferably an inorganic acid, particularly preferably hydrochloric acid.

Finally, the product can be isolated from the reaction mixture by extraction with an organic solvent and obtained as a solid by precipitation with another suitable organic solvent.

In a preferred process according to the invention the compound of formula 2a is prepared by reacting a compound of formula 3a,

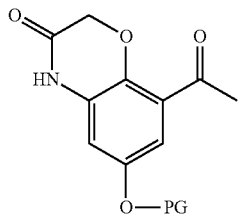

3a wherein PG has the meaning given in claim 1.

In the process according to the invention a compound of formula 3a is reacted with a halogenating reagent in a suitable solvent. Examples of suitable solvents are organic solvents. Preferred solvents are selected from among acetic acid, butyl acetate, methylene chloride, tetrahydrofuran, toluene and dioxane. Particularly preferred solvents according to the invention are tetrahydrofuran and dioxane.

In a preferred embodiment of the invention the halogenating reagent used is a brominating reagent, particularly preferably bromine, N-bromosuccinimide, benzyltrimethylammonium tribromide and tetrabutylammonium tribromide. Based on the compound 3a used, preferably at least stoichiometric amounts of halogenating reagent are used according to the invention. If required the halogenating reagent may also be used in excess, for example in amounts of up to 3 equivalents, preferably in amounts of up to 2 equivalents, particularly preferably 1 to 1.5 equivalents, based on the compound 3a used. The halogenating reagent may be added to the reaction mixture in a solvent, preferably in an organic, polar solvent, particularly preferably in methanol, ethanol and dioxane, particularly in methanol and dioxane, or in a mixture thereof, particularly in a mixture of methanol and dioxane.

The reaction is preferably carried out at a temperature of 0 to 40° C., preferably at a temperature of 10 to 30° C., particularly preferably at a temperature of 15 to 25° C.

After the halogenating reagent has been added the reaction mixture is stirred for a period of 10 min to 6 hours, preferably 30 min to 4 hours, particularly preferably 90 to 150 min.

To isolate the product water is added to the reaction mixture, wherein the mixture is cooled to a temperature of −10° C. to 10° C., preferably 0 to 10° C., particularly preferably 0 to 5° C. and stirred for a period of 10 min to 4 hours, preferably 30 min to 2 hours, particularly preferably 50 to 70 min, after the addition of the water. The product may be obtained after filtration or centrifugation and drying.

In a preferred process according to the invention the compound of formula 3a is prepared by reacting a compound of formula 4a,

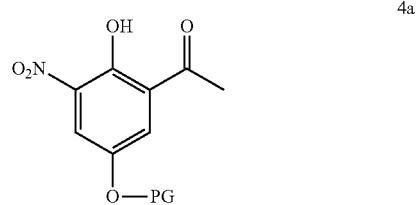

4a wherein PG has the meaning given in claim 1.

In the process according to the invention a compound of formula 4a is hydrogenated in a suitable solvent. Examples of suitable solvents are organic solvents, preferably organic, polar solvents. Particularly preferred solvents are selected from among dimethylformamide, N-methylpyrrolidinone, tetrahydrofuran, 2-methyltetrahydrofuran, toluene and dioxane. According to the invention the following are particularly preferred as solvents: dimethylformamide, tetrahydrofuran, 2-methyltetrahydrofuran and dioxane, wherein dimethylformamide and 2-methyltetrahydrofuran are of particular importance.

The hydrogenation in the process according to the invention preferably uses catalysts in the presence of hydrogen. Preferred catalysts are suitable transition metal catalysts, preferably heterogeneous transition metal catalysts, particularly preferably nickel- or platinum-containing catalysts, particularly platinum oxide.

The hydrogenation is preferably carried out in the presence of an excess of hydrogen. The latter is provided according to the invention by a hydrogen pressure of 1 bar to 10 bar, preferably from 2 to 7 bar, particularly preferably from 2.5 to 4.5 bar.

Preferably the hydrogenation is carried out at a temperature from 0 to 50° C., particularly preferably from 10 to 40° C., particularly from 20 to 30° C. After the reaction has ended the catalyst is removed from the liquid phase, preferably by filtration.

The intermediate product 4a# in the solution,

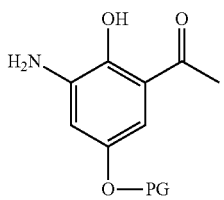

wherein PG has the meaning given in claim 1, may be isolated or further reacted directly to form a compound of formula 3a.

In accordance with the process of the invention a base, preferably a weak base, particularly preferably a carbonate, particularly potassium carbonate, is taken and the compound of formula 4a# is added in pure form or in a solution, particularly in the form of the solution filtered off from the hydrogenation catalyst in the preceding step.

Based on the compound 4a used, preferably at least twice the stoichiometric amount of the base is used according to the invention. The base may optionally also be used in excess, for example in amounts of up to 6 equivalents, preferably in amounts of up to 4 equivalents, particularly preferably about 3 to 3.5 equivalents, based on the compound 4a used.

Then chloroacetyl chloride is added to the reaction mixture. The chloroacetyl chloride is added over a period of 10 min to 2 hours, preferably 15 min to 1 hour, particularly preferably 25 to 35 min.

Based on the compound 4a used, preferably at least stoichiometric amounts of the chloroacetyl chloride are used according to the invention. If required, the chloroacetyl chloride may also be used in excess, for example in amounts of up to 4 equivalents, preferably in amounts of up to 3 equivalents, particularly preferably about 1.5 to 2 equivalents, based on the compound 4a used.

After the chloroacetyl chloride has been added the reaction mixture is stirred for a period of 10 min to 6 hours, preferably 1 to 4 hours, particularly preferably 140 to 160 min.

The reaction is preferably carried out at elevated temperature, preferably at a temperature of above 40° C., particularly preferably at a temperature of above 50° C., particularly preferably from 60° C. to 70° C.

The reaction is ended by the addition of water. The compound of formula 3a can be purified and isolated by extraction of the reaction mixture with water and subsequent recrystallisation from a suitable organic solvent. For the crystallisation it is preferable to use an aliphatic hydrocarbon, particularly preferably an aliphatic cyclic hydrocarbon, particularly cyclohexane and methylcyclohexane.

In a preferred process according to the invention, the compound of formula 4a is prepared by reacting a compound of formula 5a,

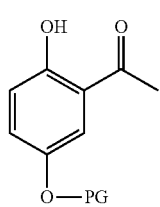

wherein PG has the meaning given in claim 1.

In the process according to the invention a compound of formula 5a is reacted with a nitrogenating reagent in a suitable solvent. Suitable solvents include organic solvents and acids, preferably organic protic solvents and acids. Particularly preferred solvents are acetic acid and sulphuric acid, particularly acetic acid.

For the nitrogenation in the process according to the invention it is preferable to use 6-65% nitric acid, as well as nitronium tetrafluoroborate or acetyl nitrate. Nitric acid, particularly 65% nitric acid, is particularly preferred.

Based on the compound 5a used, preferably at least stoichiometric amounts of the nitrogenating reagent are used according to the invention. If required the nitrogenating reagent may also be used in excess, for example in amounts of up to 2 equivalents, preferably in amounts of up to 1.5 equivalents, particularly preferably about 1 to 1.1 equivalents, based on the compound 5a used.

After the nitrogenating reagent has been added the reaction mixture is stirred over a period of 10 min to 4 hours, preferably 20 min to 3 hours, particularly preferably 40 to 80 minutes.

Then the reaction mixture is diluted with sufficient water to precipitate the compound of formula 4a from the solution. To complete the crystallisation stirring is continued for a further 20 min to 3 hours, preferably 30 min to 2 hours, particularly preferably 40-80 min, at a temperature of 0° C. to 20° C., preferably at 5° C. to 15° C., particularly preferably at 8° C. to 12° C. The compound of formula 4a may be obtained by separation from the liquid phase, preferably by filtration or centrifugation.

In a preferred process according to the invention, the compound of formula 5a is prepared by reacting a compound of formula 6a,

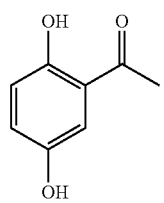

In the process according to the invention a compound of formula 6a is reacted in a suitable solvent with a protective group PG-A, wherein A denotes a suitable leaving group such as for example chlorine, bromine, iodine, methanesulphonyl, trifluoromethanesulphonyl or p-toluenesulphonyl. Preferably, a protective group is used which can be eliminated as described with reference to the cleaving of the protective group PG from compounds of formula 1a. Particularly preferably, an optionally substituted benzyl protective group is used.

In a preferred process according to the invention, the compound of formula 1b is prepared by reacting a compound of formula 2b,

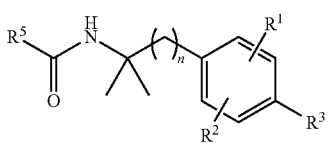

wherein $R^1$, $R^2$, $R^3$ and n have the meanings given in claims 1 to 5 and
$R^5$ denotes Me.

In the process according to the invention a compound of formula 2b is reacted with a strong base in a suitable solvent. Examples of suitable solvents include organic solvents; particularly preferred solvents are selected from among ethanol, 2-ethoxyethanol and ethyleneglycol or mixtures thereof. Particularly preferably, 2-ethoxyethanol or ethyleneglycol or a mixture thereof is used as the solvent according to the invention. Preferably, the mixture consists of equal parts by volume of 2-ethoxyethanol and ethyleneglycol, although a slight excess of one or other solvent is also possible.

The strong base used is particularly an inorganic hydroxide, preferably an alkaline earth or alkali metal hydroxide, particularly sodium hydroxide or potassium hydroxide. According to the invention potassium hydroxide is of particular importance.

Based on the compound 2b used, preferably at least stoichiometric amounts of the strong base are used according to the invention. If required the strong base may also be used in excess, for example in amounts of up to 8 equivalents, preferably in amounts of up to 6 equivalents, preferably about 2 to 4, particularly preferably 3.5 to 4.5 equivalents, based on the compound 2b used.

The reaction is preferably carried out at elevated temperature, preferably at a temperature of above 100° C., particularly preferably at a temperature of above 120° C. Particularly preferably the reaction mixture is heated to 140-160° C., particularly to 145-155° C.

Then for extraction the reaction mixture is diluted with a solvent and water. Solvents of particular interest are toluene, xylene, heptane, methylcyclohexane or tert-butyl-methyl-ether, preferably toluene or xylene. The aqueous phase is eliminated, the organic phase is extracted with water in additional purification steps. The water may be acidic, neutral or alkaline, by the use of common additives. Preferably the organic phase is extracted once with acidified water and then with basic water. The product may be obtained from the organic phase by elimination of the solvent.

In a preferred process according to the invention, the compound of formula 2b is prepared by reacting a compound of formula 3b,

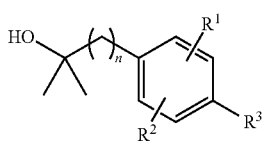

wherein $R^1$, $R^2$, $R^3$ and n have the meanings given in claims 1 to 5.

In the process according to the invention a compound of formula 3b is reacted in a suitable solvent with acetonitrile in the presence of an acid. Examples of suitable solvents are acids, preferably organic acids, while the particularly preferred solvent is acetic acid.

Based on the compound 3b used, preferably at least stoichiometric amounts of acetonitrile are used according to the invention. Preferably the acetonitrile is used in excess, for example in amounts of up to 6 equivalents, preferably in amounts of up to 5 equivalents, particularly preferably about 2 to 4 equivalents, particularly 2.5 to 3.5 equivalents, based on the compound 3b used.

The acid in whose presence the reaction is carried out is preferably sulphuric acid, formic acid, p-toluenesulphonic acid, methanesulphonic acid, perchloric acid or polyphosphoric acid, particularly preferably sulphuric acid.

Based on the compound 3b used, preferably at least stoichiometric amounts of the acid are used according to the invention. If required the acid may also be used in excess, for example in amounts of up to 2 equivalents, preferably in amounts of up to 1.5 equivalents, particularly preferably about 1 to 1.1 equivalents, based on the compound 5a used. After the acid has been added the reaction mixture is stirred for a period of 1 to 5 hours, preferably 2 to 4 hours, particularly preferably 170 to 190 min.

The reaction is preferably carried out at elevated temperature, preferably at a temperature of above 30° C., particularly preferably at a temperature of above 40° C., particularly preferably from 45° C. to 60° C. Surprisingly, it has been found that in this process no undesirable cleaving of the methyl ether function takes place as might have been expected from the literature (Can. J. Chem. 56 (1978), 3054-3058).

Then the reaction mixture is transferred into a second reactor which contains a cooled mixture of solvents. Examples of suitable solvents include mixtures of polar and non-polar solvents, preferably aqueous, organic, polar and non-polar solvents. Particularly preferred solvents as components of the mixture are selected from among water, tert-butyl-methyl-ether, tetrahydrofuran, toluene, dioxane, hexane, cyclohexane and methylcyclohexane. According to the invention it is particularly preferable to use, as ingredients of the mixture, water, tert-butylmethylether, tetrahydrofuran, toluene, cyclohexane and methylcyclohexane, while a mixture of water, tert-butylmethylether and methylcyclohexane is of particular importance.

Preferably the mixture of solvents is kept at a reduced temperature, preferably at a temperature of below 20° C., particularly preferably at a temperature below 15° C., particularly preferably 0° C. to 15° C.

In order to precipitate the product out of the solvent, the pH of the reaction mixture is raised, preferably into the basic range, particularly preferably from pH 8 to 12, particularly from pH 9 to 10. Preferably an ammonia solution is used to raise the pH value.

After the addition has ended and the pH has been adjusted the reaction mixture is stirred for a period of 10 min to 3 hours, preferably 20 min to 2 hours, particularly preferably 50 to 70 min.

Then the product is removed by centrifuging and washed with the above-mentioned solvents used for the reaction. A product of greater purity can be obtained by further recrystallisation, or precipitation, e.g. with $C_{1-8}$-alcohols and water.

In a preferred process according to the invention, the compound of formula 3b is prepared by reacting a compound of formula 4b,

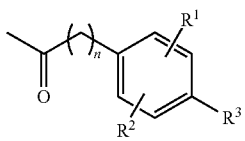

4b wherein R¹, R², R³ and n have the meanings given in claims 1 to 5.

In the process according to the invention a compound of formula 4b is subjected to a Grignard reaction in a suitable solvent with methylmagnesium bromide. Organic solvents are suitable for use as the solvent. Preferred solvents are selected from among diethyl ether, tert-butyl-methylether, tetrahydrofuran, toluene and dioxane. According to the invention it is particularly preferable to use tert-butyl-methylether, tetrahydrofuran and toluene as solvent.

The reaction is preferably carried out at ambient temperature, preferably at a temperature of 10 to 20° C., particularly preferably at a temperature of 15 to 25° C.

After the educts have been combined the reaction mixture is stirred for a period of 10 min to 3 hours, preferably 20 min to 2 hours, particularly preferably 50 to 70 min.

To stop the reaction, water and an acid, preferably sulphuric acid, are added to the reaction mixture. After extraction of the organic phase using standard methods the product may be isolated by elimination of the solvent. The purity of the product can be increased by recrystallisation from an organic non-polar solvent, preferably n-heptane.

The invention further relates to the new intermediate products of formula 3a,

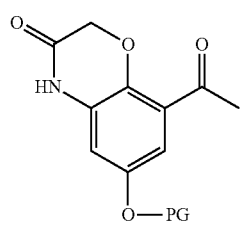

3a wherein PG has the meaning given in claim 1.

The invention further relates to the new intermediate products of formula 4a,

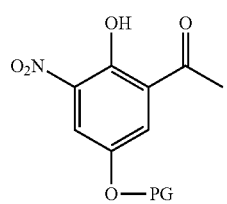

4a wherein PG has the meaning given in claim 1.

The invention further relates to the new intermediate products of formula 4a#,

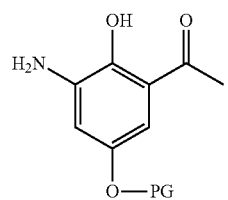

4a# wherein PG has the meaning given in claim 1.

The invention further relates to the new intermediate products of formula 2b,

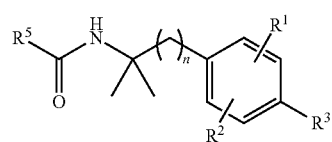

2b wherein R¹, R², R³ and n have the meanings given in claims 1 to 5 and

R⁵ denotes Me.

The subject matter of the invention also includes a process for preparing compounds of formula 2a,

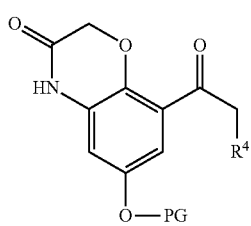

2a wherein PG has the meaning given in claim 1 and R⁴ denotes halogen, preferably bromine or chlorine, characterised in that a compound of formula 3a,

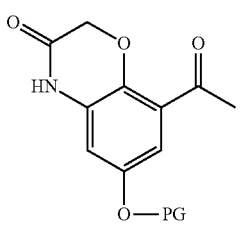

3a wherein PG has the meaning given in claim 1, is reacted with the halogenating reagent selected from among tetrabutylammonium tribromide, benzyltrimethylammonium dichloriodide, N-bromo-succinimide, N-chloro-succinimide, sulphuryl chloride and bromine/dioxane, preferably tetrabutylammonium tribromide or N-bromo-succinimide.

The subject matter of the invention also includes a process for preparing compounds of formula 3a,

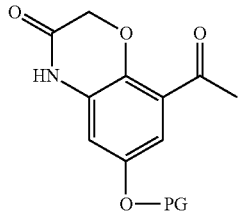

3a wherein PG has the meaning given in claim 1, characterised in that a compound of formula 4a,

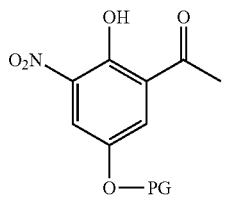

4a wherein PG has the meaning given in claim 1, is subjected to catalytic hydrogenation and then reacted with chloroacetyl chloride.

The subject matter of the invention also includes a process according to claim 16, wherein a compound of formula 4a$^\#$,

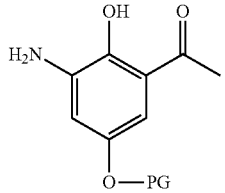

4a$^\#$ wherein PG has the meaning given in claim 1, is formed as the intermediate product of the hydrogenation.

The subject matter of the invention also includes a process for preparing compounds of formula 4a,

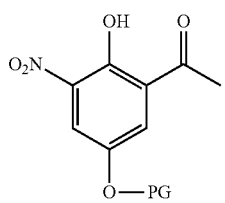

4a wherein PG has the meaning given in claim 1 and is characterised in that a compound of formula 5a,

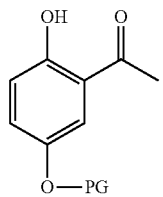

5a wherein PG has the meaning given in claim 1, is reacted with a nitrogenating reagent selected from among 65% nitric acid, potassium nitrate/sulphuric acid or nitronium tetrafluoroborate, preferably 65% nitric acid.

The subject matter of the invention also includes a process for preparing compounds of formula 1b,

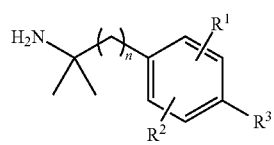

1b wherein $R^1$, $R^2$, $R^3$ and n have the meanings given in claims 1 to 5, characterised in that a compound of formula 2b,

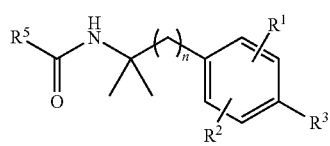

2b wherein $R^1$, $R^2$, $R^3$ and n have the meanings given in claims 1 to 5 and $R^5$ denotes Me, is reacted with a base selected from among potassium hydroxide, sodium hydroxide, lithium hydroxide and caesium hydroxide, preferably potassium hydroxide or sodium hydroxide.

The subject matter of the invention also includes a process for preparing compounds of formula 2b,

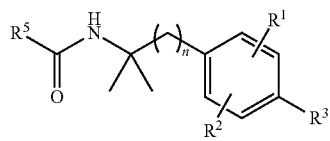

2b wherein $R^1$, $R^2$, $R^3$ and n have the meanings given in claims 1 to 5 and $R^5$ denotes Me, characterised in that a compound of formula 3b,

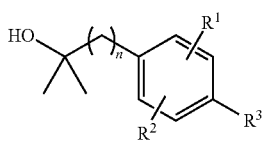

wherein $R^1$, $R^2$, $R^3$ and n have the meanings given in claims 1 to 5, is reacted with a compound of formula

wherein $R^5$ has the meaning given above, in the presence of a hygroscopic reagent selected from among sulphuric acid, formic acid, p-toluenesulphonic acid, methanesulphonic acid, perchloric acid and polyphosphoric acid, preferably sulphuric acid, and is then reacted with a base selected from among aqueous solutions of ammonia, sodium hydroxide, potassium hydroxide, sodium carbonate and potassium carbonate.

Terms And Definitions Used

By an "organic solvent" is meant, within the scope of the invention, an organic, low-molecular substance which can dissolve other organic substances by a physical method. To be suitable the prerequisite for the solvent is that neither the dissolving substance nor the dissolved substance should be chemically altered during the dissolving process, i.e. the components of the solution should be recoverable in their original form by physical separation processes such as distillation, crystallisation, sublimation, evaporation or adsorption. For various reasons, not only the pure solvents but also mixtures that combine the dissolving properties may be used. Examples include:

alcohols, preferably methanol, ethanol, propanol, butanol, octanol, cyclohexanol;

glycols, preferably ethyleneglycol, diethyleneglycol;

ethers/glycolethers, preferably diethyl ether, tert-butylmethylether, dibutylether, anisol, dioxane, tetrahydrofuran, mono-, di-, tri-, polyethyleneglycol ethers;

ketones, preferably acetone, butanone, cyclohexanone;

esters, preferably acetic acid esters, glycolesters;

amides and other nitrogen compounds, preferably dimethylformamide, pyridine, N-methylpyrrolidone, acetonitrile;

sulphur compounds, preferably carbon disulphide, dimethylsulphoxide, sulpholane;

nitro compounds, preferably nitrobenzene;

halogenated hydrocarbons, preferably dichloromethane, chloroform, tetrachlormethane, tri- and tetrachloroethene, 1,2-dichloroethane, chlorofluorocarbons;

aliphatic or alicyclic hydrocarbons, preferably benzines, petroleum ether, cyclohexane, methylcyclohexane, decaline, terpene-L.; or aromatic hydrocarbons, preferably benzene, toluene, o-xylene, m-xylene, p-xylene;

or corresponding mixtures thereof.

By the term "$C_{1-4}$-alkyl" (including those which are part of other groups) are meant branched and unbranched alkyl groups with 1 to 4 carbon atoms. Examples include: methyl, ethyl, n-propyl, iso-propyl, n-butyl, iso-butyl, sec-butyl or tert-butyl. In some cases the abbreviations Me, Et, n-Pr, i-Pr, n-Bu, i-Bu, t-Bu, etc. are also used for the above-mentioned groups. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{1-4}$-alkylene" (including those which are part of other groups) are meant branched and unbranched alkylene groups with 1 to 4 carbon atoms. Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

By the term "$C_{1-8}$-alcohol" are meant branched and unbranched alcohols with 1 to 8 carbon atoms and one or two hydroxy groups. Alcohols with 1 to 4 carbon atoms are preferred. Examples include: methanol, ethanol, n-propanol, iso-propanol, n-butanol, iso-butanol, sec-butanol or tert-butanol. In some cases the abbreviations MeOH, EtOH, n-PrOH, i-PrOH, n-BuOH, i-BuOH, t-BuOH, etc. are optionally also used for the above-mentioned molecules. Unless stated otherwise, the definitions propanol, butanol, pentanol and hexanol include all the possible isomeric forms of the groups in question. Thus for example propanol includes n-propanol and iso-propanol, butanol includes iso-butanol, sec-butanol and tert-butanol etc.

By the term "$C_{3-8}$-esters" are meant branched and unbranched esters with a total of 3 to 8 carbon atoms. Esters of acetic acid with 3 to 6 carbon atoms are preferred. Examples include: methyl acetate, ethyl acetate, n-propyl acetate, i-propyl acetate or n-butyl acetate, of which ethyl acetate is preferred.

"Halogen" within the scope of the present invention denotes fluorine, chlorine, bromine or iodine. Unless stated to the contrary, fluorine, chlorine and bromine are regarded as preferred halogens.

"Protective groups" for the purposes of the present invention is a collective term for organic groups with which certain functional groups of a molecule containing a number of active centres can temporarily be protected from attack by reagents so that reactions take place only at the desired (unprotected) sites. The protective groups should be introduced selectively under mild conditions. They must be stable for the duration of the protection under all the conditions of the reactions and purifying procedures which are to be carried out; racemisations and epimerisations must be suppressed. Protective groups should be capable of being cleaved again under mild conditions selectively and ideally in high yields. The choice of a suitable protective group, the reaction conditions (solvent, temperature, duration, etc.), and also the options for removing a protective group are known in the art (e.g. Philip Kocienski, Protecting Groups, 3rd ed. 2004, THIEME, Stuttgart, ISBN: 3131370033). Preferred protective groups are optionally substituted benzyl, diphenylmethyl, trityl, tosyl, mesyl or triflate, of which optionally substituted benzyl is particularly preferred.

EXPERIMENTAL SECTION

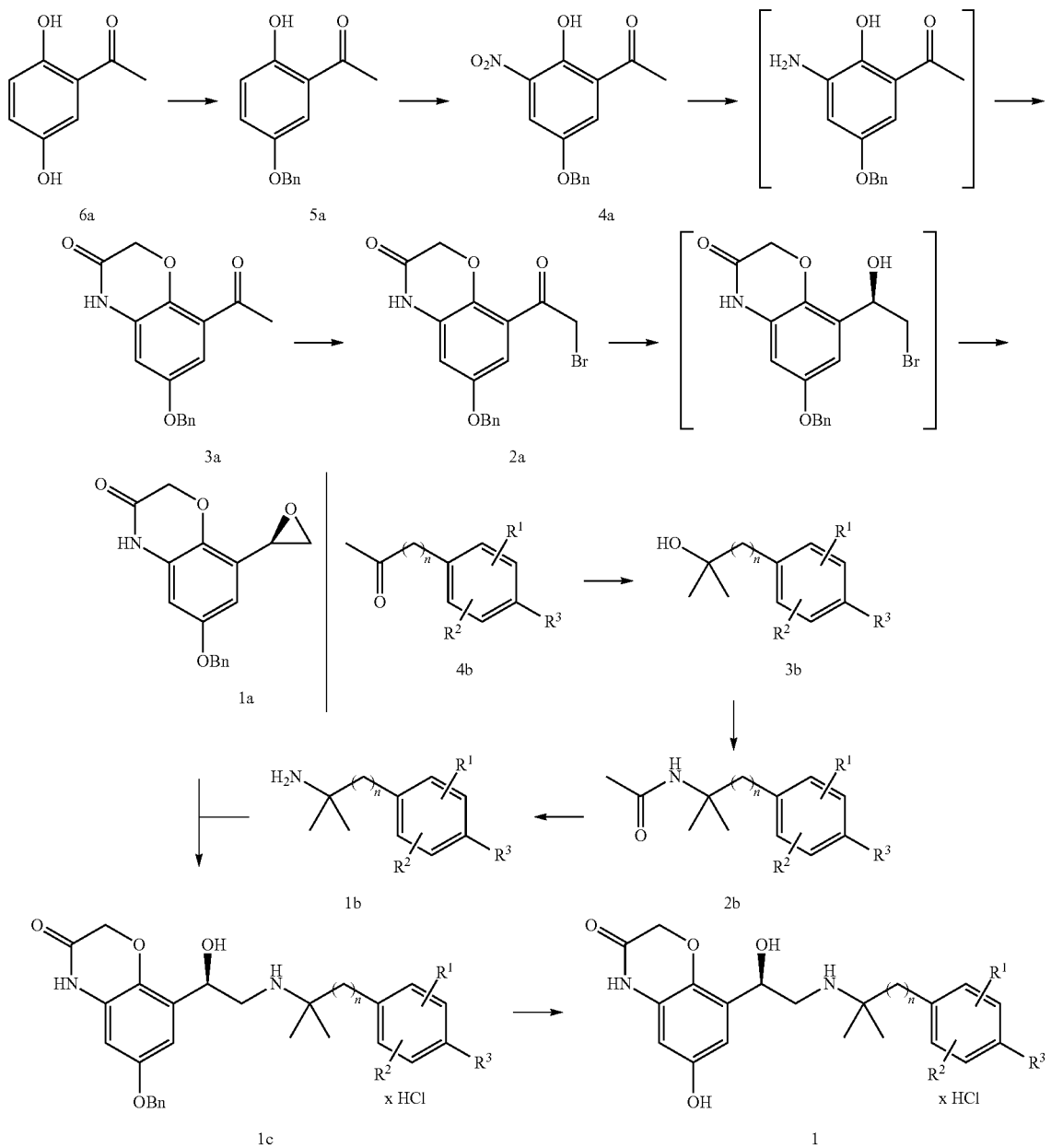

wherein Bn denotes benzyl and
n may denote 1 or 2;

$R^1$ may denote hydrogen, halogen, $C_{1-4}$-alkyl or $O-C_{1-4}$-alkyl;

$R^2$ may denote hydrogen, halogen, $C_{1-4}$-alkyl or $O-C_{1-4}$-alkyl;

$R^3$ may denote hydrogen, $C_{1-4}$-alkyl, OH, halogen, $O-C_{1-4}$-alkyl, $O-C_{1-4}$-alkylene-COOH, $O-C_{1-4}$-alkylene-COO-$C_{1-4}$-alkyl.

8-[(1R)-1-hydroxy-2-[[2-aryl-1,1-dimethyl-ethyl]-amino]ethyl]-6-(phenylmethoxy)-2H-1,4-benzoxazin-3(4H)-one-hydrochloride of formula 1c: 7.00 kg (23.54 mol) 8-(2R)-oxiranyl-6-(phenylmethoxy)-2H-1,4-benzoxazin-3(4H)-one 1a and 34.70 mol aryl-1,1-dimethyl-ethylamine of formula 1b are placed in 70 l 1,4-dioxane. The reactor contents are heated to 97° C. and stirred for 48 hours at this temperature.

Then the mixture is cooled to 40° C. and 56 l of 1,4-dioxane are distilled off in vacuo. 70 l ethanol are added to the residue, it is cooled to 25° C., and 4.15 kg (34.14 mol) hydrochloric acid (30%) are added at 25° C. within 15 minutes. Then the mixture is inoculated and stirred until crystallisation occurs. The resulting suspension is cooled to 20° C. and stirred for a further 2 hours. The product is centrifuged, washed with 21 l of ethanol and dried in vacuo at 50° C.

Yield (1c): 84-90%, enantiomer purity according to HPLC: 89.5-99.5%.

6-hydroxy-8-[(1R)-1-hydroxy-2-[[2-aryl-1,1-dimethyl-ethyl]-amino]ethyl]-2H-1,4-benzoxazin-3(4H)-one-hydrochloride of formula 1: 19.49 mol of 8-[(1R)-1-hydroxy-2-[[2-(4-methoxyphenyl)-1,1-dimethyl-ethyl]-amino]ethyl]-6-

(phenylmethoxy)-2H-1,4-benzoxazin-3(4H)-one-hydrochloride of formula 1c are placed in the hydrogenation reactor and suspended with 40 l methanol. 500 g palladium on charcoal 10% (50% water) are suspended in 17 l methanol and added to the hydrogenation reactor. The mixture is hydrogenated at 40° C. internal temperature and at 3 bar hydrogen pressure until no further uptake of hydrogen is discernible. The catalyst is filtered off and rinsed with 13.3 l methanol. 60 l of methanol are distilled off under a weak vacuum. If there is no crystal formation, the distillation residue is inoculated. Then at 50° C. 30 l i-of propanol are metered in and within 1 hour the mixture is cooled to 0° C. At 0° C. it is stirred for 1 hour, suction filtered and washed with 15 l cold i-propanol. The moist product is dissolved in 50 liters of methanol. The resulting solution is filtered clear and the pressure filter is rinsed with 10 liters of methanol. Then 52 l methanol are distilled off under a weak vacuum (about 500 mbar). If there is no crystal formation, the distillation residue is inoculated. Then 22.6 l i-propanol are metered in. The mixture is cooled to 0° C., and the suspension is stirred for 1 hour at 0° C. The suspension is suction filtered, washed with 15 liters of cold i-propanol and dried in vacuo at 50° C. Yield (1): 63-70%.

1-[2-hydroxy-5-(phenylmethoxy)-phenyl]-ethanone: 20 kg (131.4 mol) 2-acetyl-hydroquinone 6a are dissolved in 150 l methylisobutylketone and combined with 19.98 kg (144.6 mol) potassium carbonate. At 60° C., 22.48 kg (131.5 mol) benzyl bromide are added. The reaction mixture is stirred for 20 hours at 60° C. The reaction mixture is cooled to 25° C. and the solid is filtered off. The filtrate is washed twice with a solution of 0.96 kg (11.8 mol) sodium hydroxide solution (50%) and 60 l water at 25° C. The methylisobutylketone is largely distilled off in vacuo, and the residue is dissolved in 80 l methanol at 60° C. The solution is cooled to 0° C. and stirred for 1 hour at this temperature to complete the crystallisation.

Yield (5a): 24.07 kg (75.6%), chemical purity according to HPLC: 99.2%.

1-[2-hydroxy-3-nitro-5-(phenylmethoxy)-phenyl]-ethanone: 10.00 kg (41.27 mol) 1-[2-hydroxy-5-(phenylmethoxy)-phenyl]-ethanone 5a are dissolved in 50 l acetic acid. 4.40 kg (45.40 mol) nitric acid 65% are metered into this solution at 15 to 20° C. The feed vessel is rinsed with 4 l acetic acid. The reaction mixture is stirred for 1 hour. After inoculation 50 l water are added. The suspension obtained is stirred for 1 hour at 10° C. to complete the crystallisation. The product is centrifuged and dried at 50° C.

Yield (4a): 10.34 kg (87.2%), chemical purity according to HPLC: 99.0%.

8-acetyl-6-(phenylmethoxy)-2H-1,4-benzoxazin-3(4H)-one: 15.00 kg (52.22 mol) 1-[2-hydroxy-3-nitro-5-(phenylmethoxy)-phenyl]-ethanone 4a, 0.165 kg platinum (IV) oxide and 45 l 2-methyltetrahydrofuran are hydrogenated at 3 bar hydrogen pressure and an internal temperature of 25° C. until no further hydrogen uptake is discernible. The catalyst is filtered off and washed with 20 l of 2-methyltetrahydrofuran. 23.09 kg (167.09 mol) potassium carbonate are placed in another reactor, and the reaction mixture from the first reactor is added. It is rinsed with 22 l of 2-methyltetrahydrofuran. Then within 30 minutes 9.44 kg (83.55 mol) chloroacetyl chloride are metered into the suspension. After 2.5 hours reaction time at 65° C., 101 l water are added. The aqueous phase is separated off at 55° C. Then 34 l 2-methyltetrahydrofuran are distilled off from the organic phase in vacuo. After heating to reflux temperature, 180 l methylcyclohexane are metered in within 30 minutes at reflux temperature. The suspension obtained is cooled to 20° C. and stirred for another 1 hour at this temperature to complete the crystallisation. Then the precipitate is removed by centrifuging, washed with 113 l methylcyclohexane and dried at 50° C.

Yield (3a): 12.70 kg (81.8%), chemical purity according to HPLC: 98.4%.

8-(bromoacetyl)-6-(phenylmethoxy)-2H-1,4-benzoxazin-3(4H)-one: 12.00 kg (40.36 mol) 8-acetyl-6-(phenylmethoxy)-2H-1,4-benzoxazin-3(4H)-one 3a are dissolved in 108 l 1,4-dioxane. Then a solution of 24.33 kg (50.45 mol) tetrabutylammonium tribromide in 48 l of 1,4-dioxane and 12 l methanol is metered into the suspension at 20° C. The reactor contents are stirred for 2 hours at 20° C. Then 72 l water are added at 20° C. within 15 minutes. After cooling to 3° C. the mixture is stirred for 1 hour, centrifuged and washed with a mixture of 9 l of 1,4-dioxane and 4.5 l water. Then it is washed with 60 l water and dried in vacuo at 50° C.

Yield (2a): 11.29 kg (74.4%), chemical purity according to HPLC: 98.0%.

8-(2R)-Oxiranyl-6-(phenylmethoxy)-2H-1,4-benzoxazin-3(4H)-one: 12.00 kg (31.90 mol) 8-(bromoacetyl)-6-(phenylmethoxy)-2H-1,4-benzoxazin-3(4H)-one 2a are dissolved in 180 l tetrahydrofuran and cooled to −30° C. 63 kg (70.18 mol) (−)-DIP chloride in hexane 65% are metered in within 1.5 hours. The reaction mixture is stirred for 1 hour and heated to 0° C. At this temperature 11.48 kg (143.54 mol) sodium hydroxide solution (50%), mixed with 36 l water, are metered in. Then the feed vessel is rinsed with 9 l water. The pH value at the end of the addition should be 13. The mixture is heated to 20° C. and stirred for 1 hour. A mixture of 4.5 l (42.11 mol) industrial grade hydrochloric acid (30%) and 18.6 l water is metered in until a pH of 8.5 is achieved. After the addition of 84 l of ethyl acetate the mixture is heated to 30° C. After phase separation half the solvent is distilled off from the organic phase, the residue is combined with 120 l tert-butyl-methylether, cooled to 0° C. and stirred for 1 hour. The product is isolated, washed with tert-butylmethylether and dried in vacuo at 50° C.

Yield (1a): 8.06 kg (85.0%), purity of enantiomers according to HPLC: 98.3%.

Compounds of formula 3b: 24.68 kg (72.6 mol) methylmagnesium chloride (22% solution in THF) are dissolved in 35 l toluene and cooled to 16° C. At 16-22° C. a solution of 60.9 mol arylacetone of formula 4b and 10 l toluene is metered in and the mixture is stirred at 22° C. for 1 hour. The reaction solution is metered into a mixture of 45 l water and 5.22 kg (51.1 mol) sulphuric acid at a temperature of 2-17° C. The two-phase mixture is stirred, and the aqueous phase is separated off. The organic phase is washed with a solution of 1.00 kg (11.9 mol) sodium hydrogen carbonate and 11 l water. The solvent is dissolved off completely in vacuo. The residue is dissolved in 65.5 l of n-heptane. After cooling to 2° C. the reaction mixture is stirred for 3 hours at this temperature. Then the product is isolated, washed with 17.5 l of n-heptane and dried in vacuo at 25° C.

Yield (3b): 75-80%, chemical purity according to HPLC: 98.9-99.9%.

Compounds of formula 2b: 55.48 mol of 1-aryl-2-methyl-propan-2-ol of formula 3b are placed in 6.83 kg (166.44 mol) acetonitrile and 13 l acetic acid and heated to 40° C. 5.66 kg (55.48 mol) sulphuric acid are metered in at 50-55° C. Then the mixture is stirred for 3 hours at 50° C. In a second reactor 160 l water, 20 l tert-butylmethylether and 21 l methylcyclohexane are cooled to 10° C. The contents of the first reactor are transferred into the second reactor. The pH of the reactor contents is adjusted to 9.5 with about 40 l of ammonia solution (25%). The suspension is cooled to 5° C. and stirred for 1 hour at this temperature. The product is separated by centrifuging and washed with 30 l water as well as with a mixture of 7.5 l tert-butylmethylether and 7.5 l methylcyclohexane. The damp product is heated to 75° C. in 25 l ethanol (96%) and at this temperature combined with 30 l water. The solution is stirred for 15 minutes at 85° C., then cooled to 2° C. and stirred for 1 hour at this temperature. The product is isolated, washed with a mixture of 5 l water and 5 l ethanol (96%) and dried.

Yield (2b): 65-71%, chemical purity according to HPLC: 98.6-99.8%.

Compounds of formula 1b: A mixture of 45.2 mol N-[2-aryl-1,1-dimethyl-ethyl]-acetamide of formula 2b, 12.07 kg KOH (180.8 mol), 15 l ethoxyethanol and 15 l ethyleneglycol is heated to 150° C. for 12 hours. After cooling to ambient temperature the mixture is diluted with 61 l water and 31 l toluene. The phases are separated and the organic phase is washed once more with 30 l water. The organic phase is combined with 52 l water. It is acidified with 8.91 kg hydrochloric acid (90.4 mol). After phase separation the aqueous product phase is combined with 30 l toluene and made alkaline with 9.04 kg 50% NaOH (113.0 mol). After phase separation the organic product phase is evaporated down in vacuo to leave an oily residue.

Yield (1b): 69-75%, chemical purity according to HPLC: 94-96%.

In the methods described above for synthesising the compounds of formulae 3b, 2b and 1b the groups $R^1$, $R^2$ and $R^3$ may have the following meanings, for example:

|  | $R^1$ | $R^2$ | $R^3$ |
| --- | --- | --- | --- |
| Example 1 | H | H | OMe |
| Example 2 | 2-F | H | F |
| Example 3 | 3-F | 5-F | H |
| Example 4 | H | H | OEt |
| Example 5 | H | H | F |

Analogously to the preparation methods described hereinbefore it is thus possible to obtain the R-forms of the following compounds of formula 1:
6-hydroxy-8-{1-hydroxy-2-[2-(4-methoxy-phenyl)-1,1-dimethyl-ethylamino]-ethyl}-4H-benzo[1,4]oxazin-3-one;
8-{2-[2-(2,4-difluoro-phenyl)-1,1-dimethyl-ethylamino]-1-hydroxy-ethyl}-6-hydroxy-4H-benzo[1,4]oxazin-3-one;
8-{2-[2-(3,5-difluoro-phenyl)-1,1-dimethyl-ethylamino]-1-hydroxy-ethyl}-6-hydroxy-4H-benzo[1,4]oxazin-3-one;
8-{2-[2-(4-ethoxy-phenyl)-1,1-dimethyl-ethylamino]-1-hydroxy-ethyl}-6-hydroxy-4H-benzo[1,4]oxazin-3-one;
8-{2-[2-(4-fluoro-phenyl)-1,1-dimethyl-ethylamino]-1-hydroxy-ethyl}-6-hydroxy-4H-benzo[1,4]oxazin-3-one.

We claim:
1. A process for preparing a compound of formula 1,

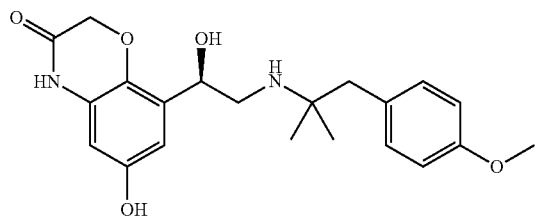

said process comprising reacting a compound of formula 2a,

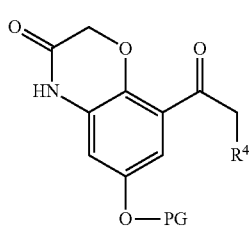

wherein PG represents a protective group and $R^4$ denotes halogen with DIP chloride in an organic solvent to obtain a compound of formula 1a;

said process further comprising reacting a compound of formula 1a,

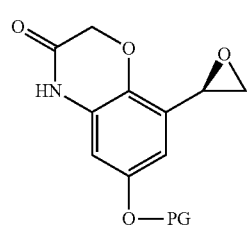

wherein PG represents a protective group, with a compound of formula 1b,

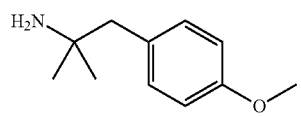

in an organic solvent to obtain a compound of formula 1c,

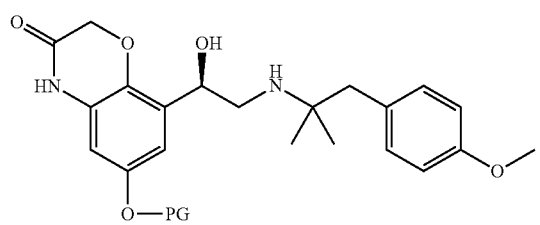

and cleaving the protective group PG to obtain the compound of formula 1.

2. A process according to claim 1, said process further comprising reacting a compound of formula 3a,

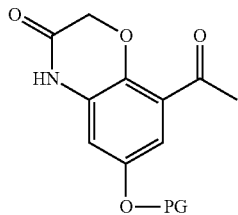

3a wherein PG has the meaning given in claim 1, with a halogenating reagent in an organic solvent to obtain the compound of formula 2a.

3. A process according to claim 1, said process further comprising reacting a compound of formula 2b with a strong base in an organic solvent,

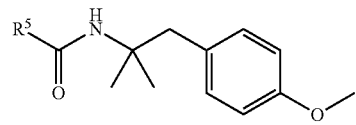

2b wherein
R⁵ denotes Me,
to obtain the compound of formula 1b.

4. A process according to claim 3, said process further comprising reacting a compound of formula 3b with acetonitrile in the presence of an acid in an organic solvent,

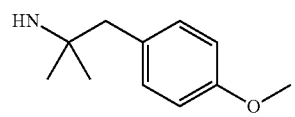

3b to obtain the compound of formula 2b.

5. A process according to claim 4, said process further comprising reacting in an organic solvent a compound of formula 4b with methylmagnesium bromide or methylmagnesium chloride,

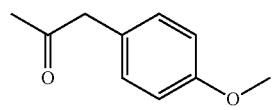

4b to obtain the compound of formula 3b.

* * * * *